United States Patent [19]

Hickling

[11] Patent Number: 5,743,867
[45] Date of Patent: Apr. 28, 1998

[54] THERAPEUTIC WRAPPING FOR A JOINT OF A PATIENT

[76] Inventor: Shawn Hickling, 5302 Verner Dr., La Palma, Calif. 90623

[21] Appl. No.: 738,894

[22] Filed: Oct. 28, 1996

[51] Int. Cl.[6] .................................................. A61F 7/00
[52] U.S. Cl. ............................. 602/65; 602/2; 602/61
[58] Field of Search ............................ 602/2, 75, 23, 602/27, 60, 61, 65, 901; 607/111, 112, 114, 108, 96

[56] References Cited

U.S. PATENT DOCUMENTS

| | | | |
|---|---|---|---|
| 3,900,035 | 8/1975 | Welch et al. | 607/108 |
| 4,055,188 | 10/1977 | Pelton | 607/112 |
| 4,676,247 | 6/1987 | Van Cleve | |
| 4,765,338 | 8/1988 | Turner et al. | 607/112 X |
| 4,938,222 | 7/1990 | Bier, Jr. | |
| 5,074,285 | 12/1991 | Wright | 602/2 X |
| 5,148,804 | 9/1992 | Hill et al. | 607/108 |
| 5,372,576 | 12/1994 | Hicks | 602/27 |
| 5,395,399 | 3/1995 | Rosenwald | 607/111 X |
| 5,409,500 | 4/1995 | Dyrek | |
| 5,415,624 | 5/1995 | Williams | |
| 5,472,414 | 12/1995 | Detty | 602/65 X |

*Primary Examiner*—Richard J. Apley
*Assistant Examiner*—Denise Pothier

[57] ABSTRACT

A therapeutic wrapping device for a limb, particular the ankle includes a wrapping member cut and sewn from an elastic fabric and defining a central strip portion with an opening for engaging over the heel and two wing portions for wrapping over the top of the ankle. Three separate bags are provided each containing a thermal gel material and each having a hook and loop fastener strip for engaging a cooperating strip on an inside of the wrapping member. The strips on the wrapping member are arranged so that two are at the top of the device spaced either side of a center line and the third is below the opening and arranged across the center line. The bags are placed over the strips so that two are arranged each on a respective side of the Achilles tendon and the third lies under the foot.

11 Claims, 4 Drawing Sheets

THERAPEUTIC WRAPPING FOR A JOINT OF A PATIENT

BACKGROUND OF THE INVENTION

This invention relates to an apparatus for therapeutic wrapping of the joint of a limb of a patient of a type which can be used for application of hot or cold treatment.

Various examples of devices of this type are shown in U.S. Pat. No. 4,676,247 (Van Cleve), U.S. Pat. No. 4,938,222 (Bier), U.S. Pat. No. 5,409,500 (Dyrek) and U.S. Pat. No. 5,415,624 (Williams). These devices can be used to provide tensioning around the joint of a limb of a patient while carrying heated or cooled packs for applying hot or cold treatment to the joint. However these devices are not fully satisfactory and that they do not properly place the treatment packs so as to apply the most effective treatment to the joint.

SUMMARY OF THE INVENTION

It is one object of the present invention, therefore, to provide an improved apparatus for therapeutic wrapping of the joint of a patient.

According to one aspect of the invention there is provided an apparatus for therapeutic wrapping of a limb of a patient, the limb having a joint with a projecting bone portion at the joint and parts of the limb above and below the joint at an angle to each other less than 180°, the apparatus comprising: a fabric wrapping member cut and sewn to form an integral body defining a central strip portion and two wing portions; the central strip portion being shaped and arranged to cover the limb at the joint such that a first part of the central strip portion lies along the limb above the joint and the second part of the central strip portion lies along the limb below the joint; the central strip portion including means defining an opening in the central strip portion between the first and second parts for engaging over the projecting bone; the first and second parts being arranged mutually at an angle less than 180° to accommodate the angle of the joint; the wing portions each projecting outwardly to a respective side of the central strip portion such that the wing portions can be wrapped around the limb to meet on the side of a limb opposite to the central strip portion, the wing portions including cooperating fastening means for applying tension to the wrapping member around the limb; at least three separate bags each containing a gel material of high thermal capacity, each bag being generally flat so as to define a front side and a rear side bounded by edges of the bag; each bag having on the rear side thereof a strip formed from one part of a hook and loop fastener material for cooperation with a respective one of three cooperating strips of hook and loop fastener material; the central strip portion having on the first part two of the cooperating strips, each arranged on a respective side of the center line of the central strip to receive a respective first and second ones of the bags; a central strip having on the second part one of the cooperating strips arranged so as to bridge the center line to receive a respective third one of the bags.

Preferably the bags are dimensioned so that the first and second bags when located on the cooperating strips substantially meet at the center line.

Preferably the third bag is dimensioned so as to substantially cover the central strip.

Preferably the bags are equal in size.

Preferably the bags are rectangular.

Preferably the bags are dimensioned such that the length of each bag is substantially equal to twice the width of each bag.

Preferably the bags are dimensioned such that, when end edges of the first and second bags are aligned with one end edge of the central strip portion, and one side edge of the third bag is aligned with an opposite end edge of the central strip portion, the bags substantially meet at said opening.

Preferably one of the wing portions includes two separate strap members which are spaced so as to leave an opening therebetween.

Preferably one of the strap members is wider than the other in a direction longitudinal of the central strip portion.

Preferably the wider strap member is arranged at a position aligned with the third bag.

Preferably the fabric wrapping member is formed of an elastic material.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
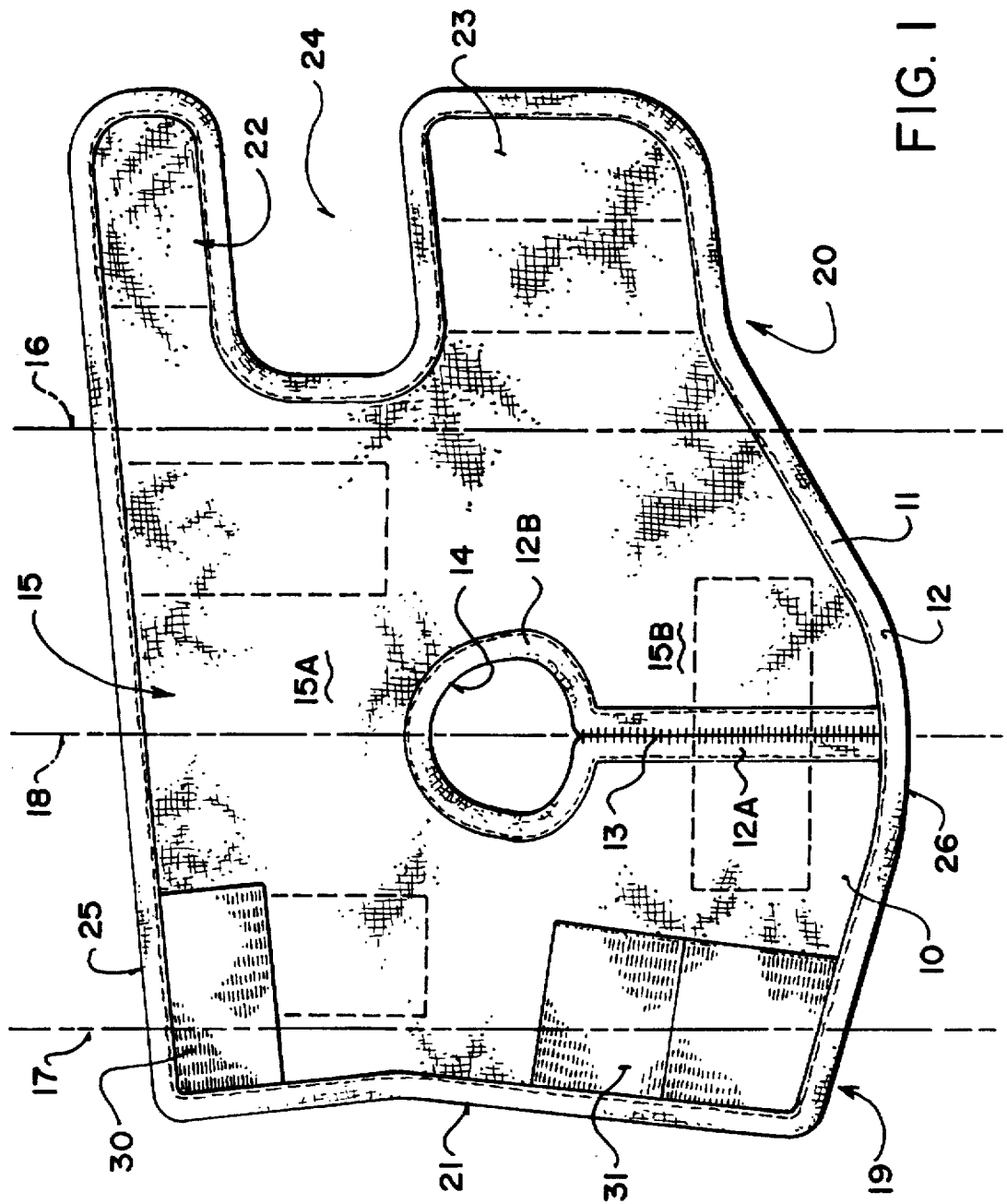
FIG. 1 is an elevational view of the apparatus according to the present invention showing an outside surface of the apparatus.

The apparatus comprises an elastic fabric layer 10 formed of a relatively thick elastic fabric such as neoprene which is cut to form an outside edge 11 with the edge 11 covered by a fabric bead 12 sewn around the full periphery of the fabric layer.

The fabric is cut and jointed along a stitched joint line 13. The fabric is cut to form the joint line 13 and the hole 14 is again surrounded by the bead portions as indicated at 12A and 12B.

A part of the material in wedge shape is removed at the joint line 13 so that when the two parts of the fabric are brought together at the joint line 13 the part of the fabric underneath the hole 14 lies at an angle to a part of the fabric above the hole 14.

The fabric is cut and shaped to form a central strip portion 15 defined between two imaginary lines 16 and 17 of the central strip portion and defining a center line 18 of the central strip portion. It will of course be appreciated that the lines 16, 17 and 18 are imaginary lines and are used in this description for purposes of clarity since the fabric member is of course an integral structure.

Outside of the lines 16 and 17 is defined a pair of wing sections 19 and 20 which are shaped to engage around the joint and to provide an overlap on the side of the joint opposite to the center line 18. One of the wing sections has a generally straight side edge 21 while the other of the wing sections has a pair of flaps 22 and 23 separated by an open area 24.

Figure 4:
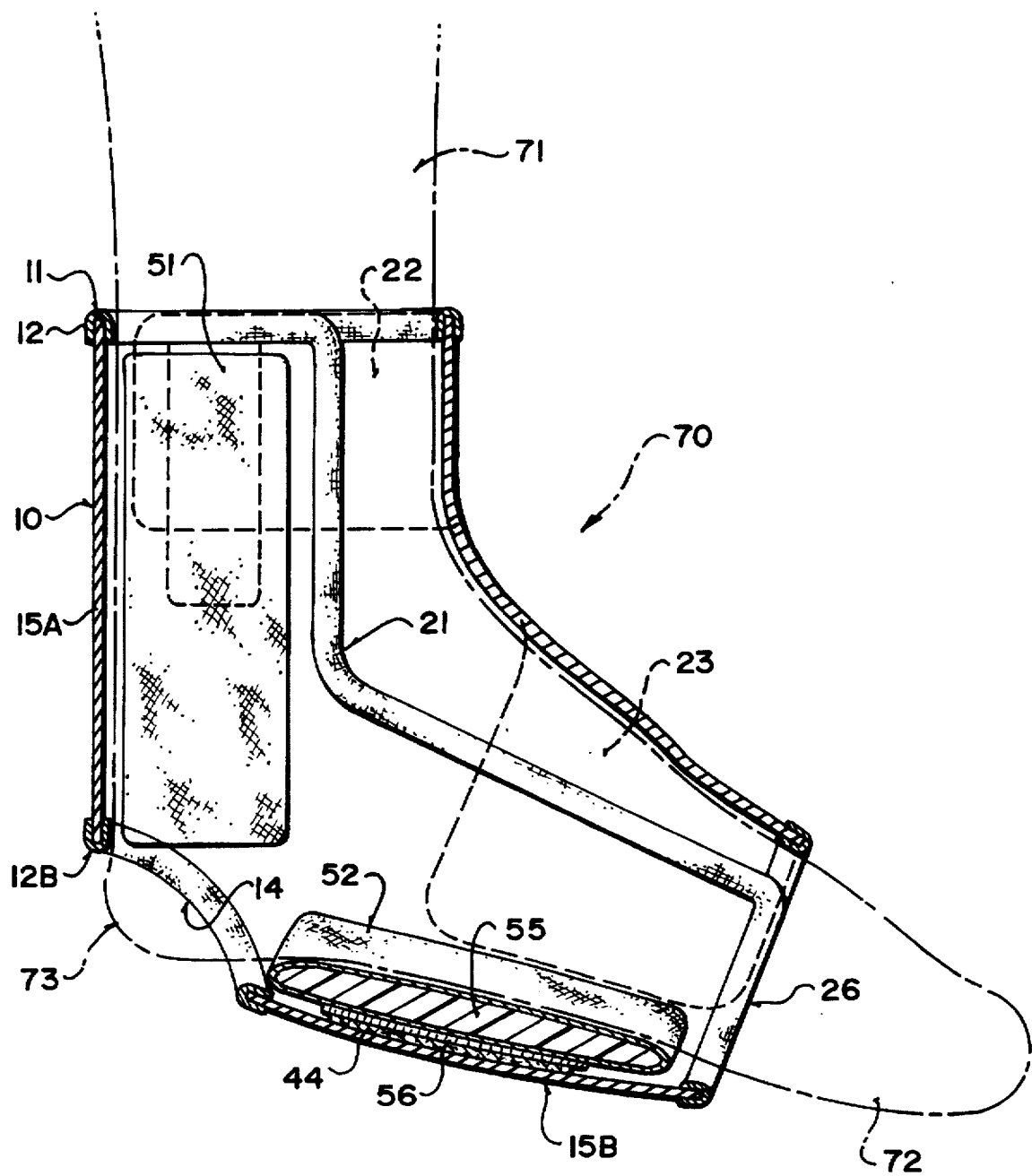
FIG. 4 is a vertical cross sectional view through the ankle joint of a patient with the apparatus of FIGS. 1, 2 and 3 wrapped around the joint, the joints being shown in chain dot line so as to expose the inside surface of the apparatus.

The fabric body 10 has a top edge 25 and a bottom edge 26 which are substantially straight but the bottom edge 26 is shown as curved since the apparatus is not planar but instead the bottom part below the hole curves away from the top part as best shown in FIG. 4.

The central strip 15 thus forms an upper part 15A above the hole 14 and a lower part 15B below the hole 14. Again it will be appreciated that these parts are in effect imaginary and are described herein for convenience.

The height of the upper part 15A from the hole 14 to the top edge 25 is substantially equal to the height of the bottom part 15B from the hole to the bottom edge 26. The width of the central strip 15 is sufficient to wrap around the majority of the limb of the patient leaving portions of the wing portions overlapping for cooperating attachment to hold the central strip portion wrapped around the joint.

On the outside surface shown in FIG. 1, the wing portion 19 carries two strips 30 and 31 of hook and loop fastener material. The strips on the outside surface of FIG. 1 are of the hook variety for attachment to the loop variety shown in FIG. 2. The strips 30 and 31 are arranged at the junctions between the side edge 21 and the top and bottom edges 25 and 26 respectively. The height of the strip 30 is so as to substantially match the height of the flap 22. The height of the strip 19 is similarly arranged to match the height of the flap 23. The flap 23 is substantially twice the height of the flap 22.

Figure 2:
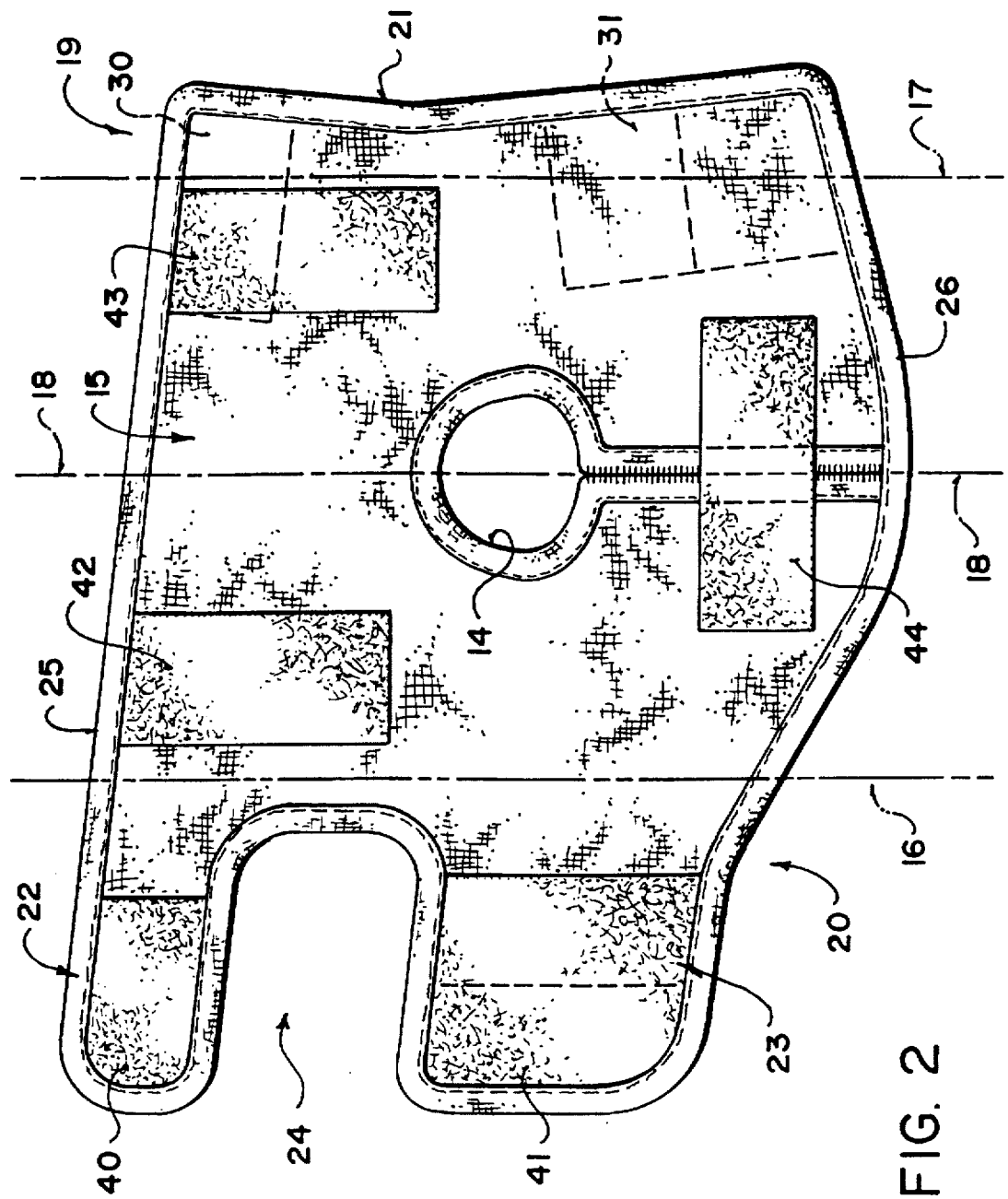
FIG. 2 is an elevational view similar to that of FIG. 1 showing the inside surface.

On the inside surface as shown in FIG. 2 is provided a plurality of strips of the loop section of the hook and loop fastener materials. Thus each of the flap members 22 and 23 is covered on the inside surface by a strip 40, 41 respectively of the loop material. In addition three strip portions 42, 43 and 44 of the loop material are applied on the central strip portion 15. Each of the strip portions 42, 43 and 44 has a length greater than the width thereof and is generally rectangular. The two strip portions 42 and 43 are arranged on either side of the center line 18 spaced outwardly from the center line and located adjacent the lines 16 and 17. The strip portions 42 and 43 lie longitudinally along the sides with the upper edge of the strip portions at the upper edge 25. The third strip portion 44 is arranged in the opposite direction so that its length is transverse to the center line 18 with the strip portion 44 bridging the center line at a position approximately midway between the lower edge of the opening 14 and the bottom edge 26.

Each of the strip portions 42, 43 and 44 of hook and loop fastener material is attached to the fabric body 10 by stitches so that the stitch lines are visible on the opposite side of the fabric as shown in FIGS. 1 and 2.

Figure 3:
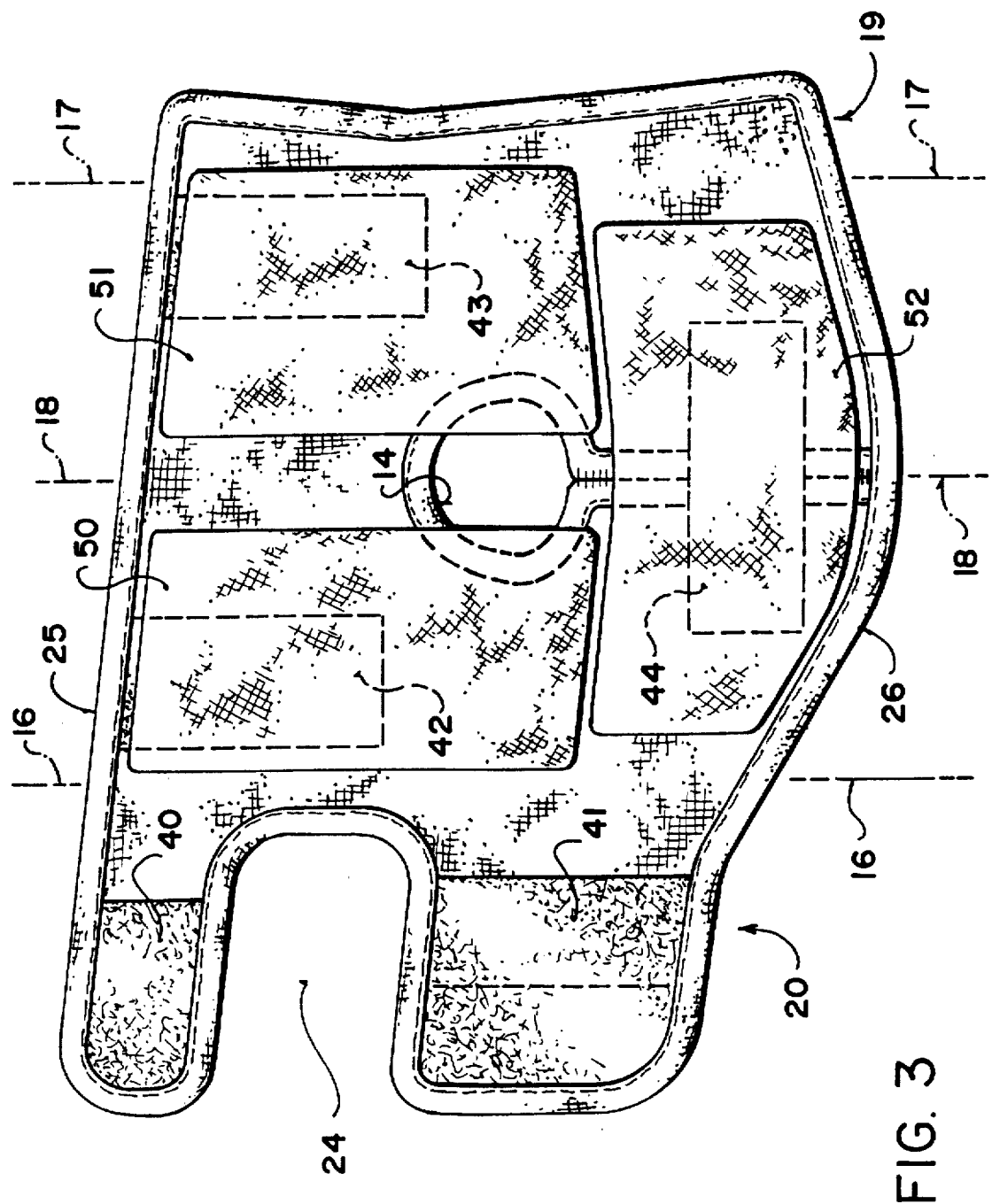
FIG. 3 is an elevational view which is the same as that of FIG. 2 including the application of the gel packs.

The apparatus further includes three gel packs 50, 51 and 52. Each of these gel packs comprises a fabric bag formed of a substantially waterproof fabric stitched along three side edges to form a fully enclosed bag containing a gel material 55. The bag is formed so that it is relatively flat with a front face, a rear face and four side edges so that the pack is substantially rectangular as shown in FIG. 3 with a width which is approximately one half of the length of the pack. On the rear face of the pack is attached a strip 56 of the hook version of the hook and loop fastener fabric for cooperation with a respective one of the strips 42, 43 and 44.

The gel packs can thus be readily removed from the fabric body simply by separating the hook and loop fastener materials so that the gel packs can be heated or cooled as required.

The dimensions of the gel packs as best shown in FIG. 3 is such that when attached onto the strips 42, 43 and 44 respectively, the two upper gel packs 50 and 51 extend from the top edge 25 to a position just below the region 15A. The gel packs further extend from the lines 16 and 17 of the center strip to a position closely adjacent or substantially meeting at the center line 18. The gel pack 52 is arranged transversely of a center line so as to bridge the center line and extend substantially from the line 16 and 17 and also from the bottom of the hole 14 to the bottom edge 26. Thus substantially the opening of the central strip is covered by the gel packs and the gel packs are conveniently arranged so that they locate against the portions of the joint in a manner which obtains the best cooling effect.

In particular the arrangement is best shown in FIG. 4 in which the apparatus is wrapped around the ankle joint 70 of the leg of a patient. The ankle joint includes an upper part 71 which is the lower leg and a foot 72 with the heel 73 projecting through the opening 14. The upper portion 15A thus lies along the rear of the leg 71 and a lower portion 15B lies along the underside of the foot. The central strip wraps around the rear of the leg and the flaps 22 and 23 wrap around the front of the leg and overlap as shown. The wider flap 23 is arranged to wrap around the foot so that the transverse pack 52 which is aligned with the wing 41 lies underneath the foot at the rear part just in front of the heel and wraps around the sides of the foot to partly come up from the sole to the sides as shown in FIG. 4. The packs 50 and 51 meet at the center line which lies directly along the center of the rear of the leg and lie to each side of the Achilles tendon.

The device has the following advantages:

1. The particular arrangement of the gel packs ensures that the important parts of the joint are directly and continually contacted.
2. The use of the hook and loop fastener for the packs within the inside of the fabric body allows some movement of the packs to provide increased contact at particular areas of the foot as required.
3. Additional packs can be provided and can be applied inside the wrapping loosely if required.
4. The packs can be readily removed and heated or cooled separately so that additional packs can be applied when the first packs have lost their heating or cooling effect.
5. The shape of the fabric including the angled upper and lower portions and the shape and arrangement of the overlapping flaps ensures an effective tensioning of the packs around the joint.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. Apparatus for therapeutic wrapping of a limb of a patient, the limb having a joint with a projecting bone portion at the joint and parts of the limb above and below the joint at an angle to each other less than 180°, the apparatus comprising:

a fabric wrapping member cut and sewn to form an integral body defining central strip portion and two wing portions;

the central strip portion being shaped and arranged to cover the limb at the joint such that a first part of the central strip portion lies along the limb above the joint and a second part of the central strip portion lies along the limb below the joint;

the central strip portion having an opening in the central strip portion between the first and second parts for surrounding the projecting bone;

the first and second parts being arranged mutually at an angle less than 180° to accommodate the angle of the joint;

the wing portions each projecting outwardly from opposite sides of the central strip portion such that the wing portions can be wrapped around the limb to meet on the side of a limb opposite to the central strip portion, the wing portions including cooperating fastening means for applying tension to the wrapping member around the limb;

at least three separate bags each containing a gel material of high thermal capacity, each bag being generally flat so as to define a front side and a rear side bounded by edges of the bag;

each bag having on the rear side thereof a strip formed from one part of a hook and loop fastener material for cooperation with a respective one of three cooperating strips of hook and loop fastener material;

the central strip portion having on the first part two of the cooperating strips, each arranged on a respective side of the center line of the central strip, to receive two of the separate bags;

the central strip portion having on the second part one of the cooperating strips arranged so as to bridge the center line to receive one of the separate bags.

2. The apparatus according to claim 1 wherein the bags are arranged so that the two of the bags located on the first part of the central strip portion substantially meet at the center line when located on the cooperating strips.

3. The apparatus according to claim 1 wherein the the one of the bags located on the second part of the central strip portion is arranged so as to substantially cover the second part.

4. The apparatus according to claim 1 wherein the bags are equal in size.

5. The apparatus according to claim 1 wherein the bags are rectangular.

6. The apparatus according to claim 5 wherein the bags are dimensioned such that the length of each bag is substantially equal to twice the width of each bag.

7. The apparatus according to claim 1 wherein the central strip portion has a top edge and bottom edge and the at least three separate bags have side edges along their length and end edges along their width, the bags are arranged such that each bags substantially meets at said opening, when one of the end edges of each of the two of the bags located on the first part is aligned with the top edge of the central strip portion and one of the side edged of the one of the bags located on the second part is aligned with the bottom edge of the central strip portion.

8. The apparatus according to claim 1 wherein one of the wing portions includes two separate strap members which are spaced so as to leave an opening therebetween.

9. The apparatus according to claim 8 wherein one of the strap members is wider than the other in a direction longitudinal to the central line of the central strip portion.

10. The apparatus according to claim 9 wherein the wider strap member is arranged at a position aligned with the one bag located on the second part.

11. The apparatus according to claim 1 wherein the fabric wrapping member is formed of an elastic material.

* * * * *